US009907554B2

(12) United States Patent
Morgan et al.

(10) Patent No.: US 9,907,554 B2
(45) Date of Patent: Mar. 6, 2018

(54) DEVICES AND METHODS FOR STABILIZING FASTENERS POST-DEPLOYMENT

(71) Applicant: Ethicon Endo-Surgery, Inc., Cincinnati, OH (US)

(72) Inventors: Jerome R. Morgan, Cincinnati, OH (US); Frederick E. Shelton, IV, Hillsboro, OH (US); Emily A. Schellin, Cincinnati, OH (US); Jeffrey S. Swayze, Hamilton, OH (US); Gary W. Knight, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 646 days.

(21) Appl. No.: 14/474,653

(22) Filed: Sep. 2, 2014

(65) Prior Publication Data

US 2016/0058445 A1    Mar. 3, 2016

(51) Int. Cl.
| | |
|---|---|
| *A61B 17/068* | (2006.01) |
| *A61B 17/072* | (2006.01) |
| *A61B 17/064* | (2006.01) |
| *A61B 90/00* | (2016.01) |

(52) U.S. Cl.
CPC .... *A61B 17/07207* (2013.01); *A61B 17/0644* (2013.01); *A61B 2017/0725* (2013.01); *A61B 2017/07228* (2013.01); *A61B 2017/07278* (2013.01); *A61B 2017/07285* (2013.01); *A61B 2090/037* (2016.02)

(58) Field of Classification Search
CPC .......... A61B 17/07207; A61B 17/0644; A61B 2090/037; A61B 2017/07228; A61B 2017/007278; A61B 17/068

USPC ............................................ 227/177.1, 175.1
See application file for complete search history.

(56) References Cited

U.S. PATENT DOCUMENTS

| | | | |
|---|---|---|---|
| 5,465,895 A | 11/1995 | Knodel et al. | |
| 5,725,536 A | 3/1998 | Oberlin et al. | |
| 6,254,615 B1 * | 7/2001 | Bolduc ............... | A61B 17/064 606/142 |
| 7,000,818 B2 | 2/2006 | Shelton, IV et al. | |
| 7,473,258 B2 | 1/2009 | Clauson et al. | |
| 7,533,790 B1 | 5/2009 | Knodel et al. | |
| 7,641,671 B2 | 1/2010 | Crainich | |

(Continued)

FOREIGN PATENT DOCUMENTS

EP    2891460 A1    7/2015

OTHER PUBLICATIONS

"MicroCutter XCHANGE™ 30." Inservice Poster. (Oct. 13).

(Continued)

*Primary Examiner* — Michelle Lopez
(74) *Attorney, Agent, or Firm* — Mintz Levin Cohn Ferris Glovsky and Popeo, P.C.

(57) ABSTRACT

Devices and methods are provided for stabilizing fasteners post-deployment. In general, the devices and methods can allow fasteners to resist counter rotation after being deployed. A fastener can be configured to resist counter rotation in a variety of ways. In some embodiments, a staple can include one or more anti-rotation mechanisms configured to resist counter rotation of the staple when the staple is deployed in tissue. In some embodiments, an orientation of a fastener relative to an orientation of one or more fasteners deployed adjacent thereto can be configured to help prevent counter rotation.

10 Claims, 10 Drawing Sheets

(56) References Cited

U.S. PATENT DOCUMENTS

| | | | |
|---|---|---|---|
| 7,669,746 B2 | 3/2010 | Shelton, IV | |
| 7,678,121 B1 | 3/2010 | Knodel | |
| 7,753,250 B2 | 7/2010 | Clauson et al. | |
| 7,918,376 B1 | 4/2011 | Knodel et al. | |
| 7,954,683 B1 | 6/2011 | Knodel et al. | |
| 7,963,432 B2 | 6/2011 | Knodel et al. | |
| 7,988,026 B2 | 8/2011 | Knodel et al. | |
| 8,056,789 B1 * | 11/2011 | White | A61B 17/0644 227/176.1 |
| 8,066,720 B2 | 11/2011 | Knodel et al. | |
| 8,070,034 B1 | 12/2011 | Knodel | |
| 8,070,036 B1 | 12/2011 | Knodel | |
| 8,087,562 B1 | 1/2012 | Manoux et al. | |
| 8,123,795 B1 | 2/2012 | Knodel et al. | |
| 8,261,958 B1 | 9/2012 | Knodel | |
| 8,272,551 B2 | 9/2012 | Knodel et al. | |
| 8,317,071 B1 | 11/2012 | Knodel | |
| 8,317,072 B1 | 11/2012 | Knodel et al. | |
| 8,356,740 B1 | 1/2013 | Knodel | |
| 8,357,174 B2 | 1/2013 | Roth et al. | |
| 8,365,973 B1 | 2/2013 | White et al. | |
| 8,403,956 B1 | 3/2013 | Thompson et al. | |
| 8,439,245 B2 | 5/2013 | Knodel et al. | |
| 8,439,246 B1 | 5/2013 | Knodel | |
| 8,496,155 B2 | 7/2013 | Knodel | |
| 8,505,800 B1 | 8/2013 | Knodel et al. | |
| 8,556,153 B1 | 10/2013 | Knodel | |
| 8,631,992 B1 * | 1/2014 | Hausen | A61B 17/0644 227/175.1 |
| 8,636,189 B1 | 1/2014 | Knodel et al. | |
| 8,662,369 B1 * | 3/2014 | Manoux | A61B 17/068 227/175.1 |
| 8,679,155 B2 | 3/2014 | Knodel et al. | |
| 8,701,960 B1 | 4/2014 | Manoux et al. | |
| 2005/0033329 A1 * | 2/2005 | Bombard | A61B 17/1152 606/153 |
| 2009/0065552 A1 | 3/2009 | Knodel et al. | |
| 2010/0155453 A1 | 6/2010 | Bombard et al. | |
| 2010/0256675 A1 * | 10/2010 | Romans | A61B 17/0644 606/219 |
| 2011/0204120 A1 | 8/2011 | Crainich | |
| 2012/0010652 A1 | 1/2012 | Hahnen et al. | |
| 2013/0277410 A1 | 10/2013 | Fernandez et al. | |
| 2014/0041191 A1 | 2/2014 | Knodel | |
| 2014/0175146 A1 | 6/2014 | Knodel | |
| 2015/0351758 A1 | 12/2015 | Shelton, IV | |

OTHER PUBLICATIONS

"MicroCutter XCHANGE™ 30." Instructions for Use. (2014).
"MicroCutter XCHANGE® 30 Videos." Cardica. Web. May 7, 2014. http://www.cardica.com/inservice-guide.php.
"MicroCutter XCHANGE® 30: The World's First and Only Articulating 5mm Stapler." Cardica. Web. May 7, 2014. http://www.cardica.com/minimally-invasive-surgery.php.
European Search Report for Application No. 15183383.7 dated Jun. 14, 2016.

* cited by examiner

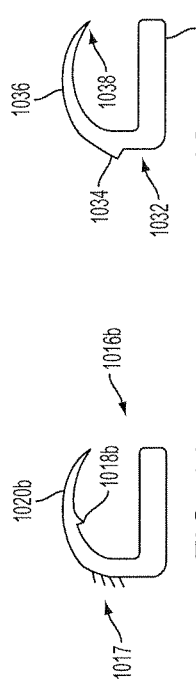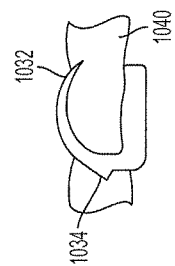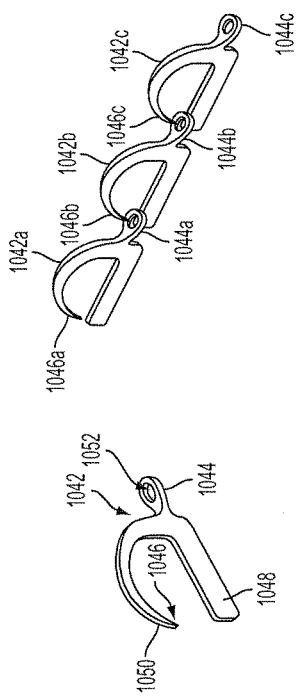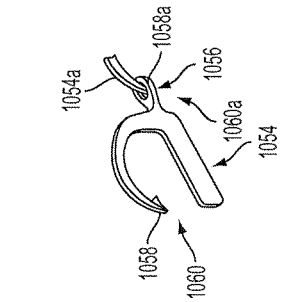

DEVICES AND METHODS FOR STABILIZING FASTENERS POST-DEPLOYMENT

FIELD OF THE INVENTION

The present disclosure relates generally to stabilizing fasteners post-deployment.

BACKGROUND

Minimally invasive surgical instruments are often preferred over traditional open surgical devices due to the reduced post-operative recovery time and minimal scarring associated with minimally invasive procedures. Laparoscopic surgery is one type of minimally invasive surgery (MIS) procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. Endoscopic surgery is another type of MIS procedure in which elongate flexible shafts are introduced into the body through a natural orifice.

Due to the benefits associated with minimally invasive surgeries, significant efforts have gone into developing a range of endoscopic and laparoscopic surgical instruments that are suitable for precise placement of a distal end effector at a desired surgical site. These distal end effectors engage the tissue in a number of ways to achieve a diagnostic or therapeutic effect (e.g., grasper, cutter, stapler, clip applier, access device, drug/gene therapy delivery device, and energy device using ultrasound, radiofrequency, laser, etc.).

For example, staplers including end effectors for grasping tissue have been developed which secure tissue between two jaws. Staples contained in one of the jaws can be driven into the grasped tissue and deformed to hold the tissue by impinging on the other jaw. The staples can form a predetermined pattern (e.g., one or more lines of staples) based upon the configuration of the staples in the one of the jaws. The stapler can be a linear stapler, in which the predetermined pattern includes one or more longitudinal lines of staples. Though staplers can be effective to grasp and staple tissue, it can be difficult to grasp and/or staple the tissue based on a variety of factors, such as a size and/or shape of the staple, a thickness and/or toughness of the tissue, etc.

Some staplers can be refilled after firing staples. In some staplers, the staples can be contained in a cartridge which can be removable from the stapler's jaw to allow the stapler to be refilled with staples contained in another cartridge inserted into the jaw. However, this refilling of cartridges can be difficult since the cartridges can be relatively small and accordingly difficult to manipulate and/or properly secure within the jaw. Refilling a stapler with a new cartridge can thus be time consuming and/or can result in an improperly loaded cartridge that can misfire staples or otherwise function improperly during use on a patient.

Accordingly, there remains a need for improved methods and devices for stapling tissue.

SUMMARY

A surgical fastening device comprises an elongate shaft having an end effector coupled to a distal end thereof, wherein the end effector includes first and second opposed jaws coupled to one another and configured to engage tissue therebetween. The device also includes a staple cartridge disposed within the first jaw. The staple cartridge includes a plurality of D-shaped, plastically deformable staples, each staple being configured to rotate in a first direction into tissue engaged between the first and second jaws. Each staple has an anti-rotation mechanism configured to prevent rotation in a second direction opposite to the first direction when the staples are deployed in tissue. Each D-shaped staple of the device includes a first leg that is substantially straight, and a second leg that is curved.

The anti-rotation mechanism can take a variety of forms. In one aspect the anti-rotation mechanism comprises a barb formed on the staple and oriented in a direction to prevent counter-rotation of the staples. For example, the anti-rotation mechanism on each staple can comprise a barb is formed on an outer-facing surface of the second leg, which may be oriented towards the first leg. In another aspect the anti-rotation mechanism comprises a coupling element formed on each staple and configured to receive a tip of an adjacent staple when deployed such that counter-rotation of the staples is prevented. In yet another aspect, the anti-rotation mechanism on each staple comprises a hoop formed adjacent to an intersection between the first and second legs and configured to receive a tip of the first leg when the staples are deployed in tissue.

The plurality of staples can be attached to a carrier. The staples can be frangibly attached to the carrier and they can be arranged in longitudinal rows on the carrier.

In another embodiment, a surgical fastening device for treating tissue can comprise a handle, an elongate shaft extending distally from the handle, and an end effector coupled to a distal end of the elongate shaft, wherein the end effector has a jaw and an anvil pivotally connected to the jaw such that the jaw and the anvil being configured to engage tissue therebetween. The fastening device also includes a plurality of fasteners disposed within the jaw, wherein the fasteners are rotatable about a pivot point. Further, the device includes a sled slidable through the jaw such that distal advancement of the sled causes each of the plurality of fasteners to rotate into tissue engaged between the jaw and the anvil. Each fastener includes an anti-rotation feature configured to prevent counter-rotation of the fasteners when deployed in tissue.

In one aspect, the anti-rotation feature comprises a barb formed on the fastener and oriented in a direction to prevent counter-rotation of the fasteners. Each fastener can include a straight leg and a curved leg, and the barb can be formed on an outer surface of the curved leg so as to be oriented toward the straight leg. In another aspect, the anti-rotation feature comprises a coupling element formed on each fastener and configured to receive a tip of an adjacent fastener when deployed such that counter-rotation of the fasteners is prevented. By way of example, the coupling element can be in the form of a hoop formed on the fastener.

The fasteners can be attached to a carrier in such a way that they are frangibly attached thereto. Further, the fasteners can be arranged in longitudinal rows.

BRIEF DESCRIPTION OF THE DRAWINGS

This invention will be more fully understood from the following detailed description taken in conjunction with the accompanying drawings, in which:

FIG. 14 is a side view of an embodiment of a fastener including first and second anti-rotation mechanisms;

FIG. 15 is a side view of another embodiment of a fastener including an anti-rotation mechanism;

FIG. 16 is a side, partially transparent view of the fastener of FIG. 15 deployed in tissue;

FIG. 17 is a perspective view of another embodiment of a fastener including an anti-rotation mechanism;

FIG. 18 is a perspective view of an embodiment of a plurality of interconnected deployed fasteners;

FIG. 19 is a perspective view another embodiment of a fastener including a first anti-rotation mechanism and a second anti-rotation mechanism, with the first anti-rotation mechanism coupled to an adjacent fastener;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Figure 1:
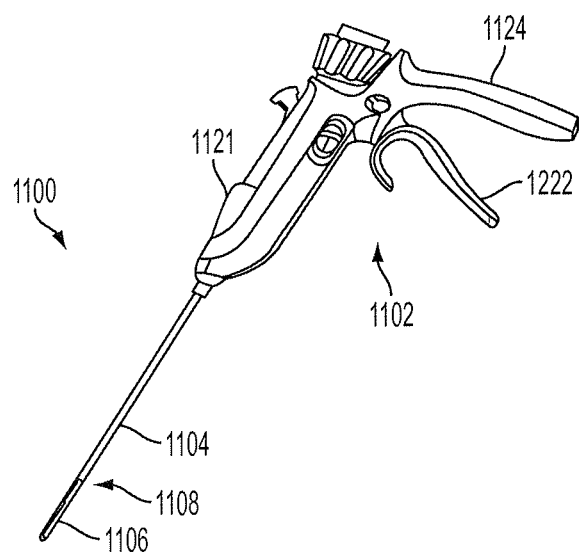
FIG. 1 is a perspective view of one embodiment of a surgical device configured to apply fasteners to tissue and including an end effector, the end effector being in a closed position.

FIG. 1 illustrates one embodiment of a surgical device 1100 that can be configured to apply staples to tissue. The device 1100 in this illustrated embodiment includes a linear stapler configured to apply linear rows of staples. Other embodiments of surgical devices that can be configured to apply staples to tissue are described in U.S. Pat. No. 5,465,895 entitled "Surgical Stapler Instrument" filed Feb. 3, 1994, U.S. Pat. No. 7,000,818 entitled "Surgical Stapling Instrument Having Separate Distinct Closing And Firing Systems" filed May 20, 2003, U.S. Pat. No. 7,669,746 entitled "Staple Cartridges For Forming Staples Having Differing Formed Staple Heights" filed on Aug. 31, 2005, and U.S. Pat. Pub. No. 2014/0175146 entitled "Microcutter Stapling Apparatus Clamp And Deploy Mechanisms Systems And Methods" filed Dec. 19, 2013, which are hereby incorporated by reference in their entireties.

Figure 2:
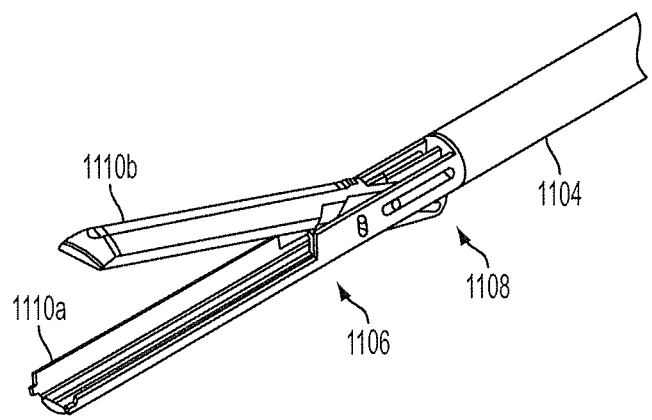
FIG. 2 is a perspective view of the end effector of FIG. 1 in an open position.
Figure 3:
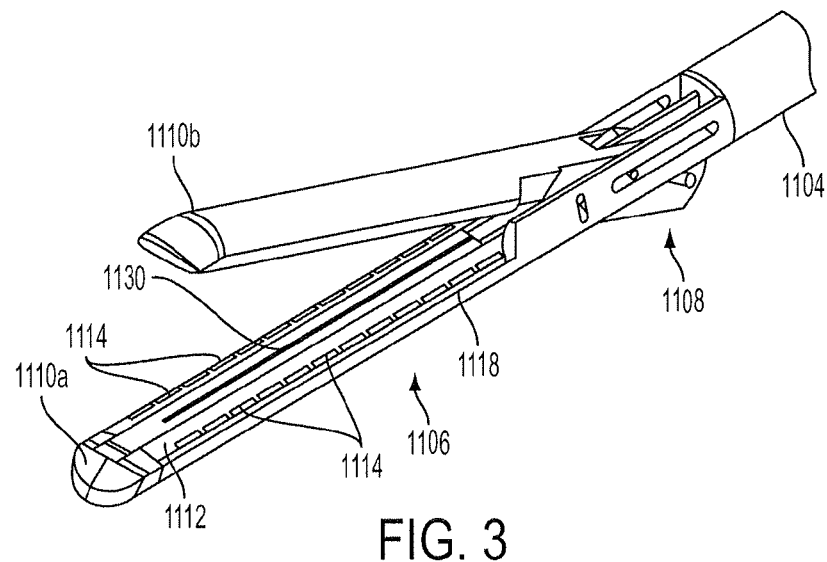
FIG. 3 is a perspective view of the end effector of FIG. 2 with one embodiment of a cartridge removably coupled thereto.

Referring again to FIG. 1, the device 1100 can include a proximal handle portion 1102 having an elongate shaft 1104 extending distally therefrom. As also shown in FIG. 2 and FIG. 3, the shaft 1104 can have an end effector 1106 coupled to a distal end thereof. The end effector 1106 can be coupled to the shaft 1104 at a pivot joint 1108. A proximal end of the end effector 1106 can be pivotally coupled to the joint 1108 at a distal end of the shaft 1104. The end effector 1106 in this illustrated embodiment includes a tissue grasper having a pair of opposed first and second jaws 1110a, 1110b configured to move between open and closed positions. The first jaw is also referred to herein as a "bottom jaw" and a "cartridge jaw," and the second jaw is also referred to herein as an "upper jaw" and an "anvil." As discussed further below, the handle portion 1102 can be configured to be manipulated to effect the opening and closing of the opposed jaws 1110a, 1110b, e.g., movement of one or both the jaws 1110a, 1110b about the pivot joint 1108, and the handle portion 1102 can be configured to be manipulated to effect the firing of staples (not shown) from a one of the jaws 1110a, 1110b, e.g., a bottom or cartridge one of the jaws 1110a. The staple firing can be independent of the opening and closing of the jaws 1110a, 1110b.

The handle portion 1102 can have a variety of sizes, shapes, and configurations. The handle portion 1102 can include a main housing 1121, which can house a variety of elements therein and can have some elements accessible outside thereof, such as a movable trigger 1122 and a stationary handle 1124. The movable trigger 1122 can be configured to be manually manipulated to move the movable trigger 1122 relative to the stationary handle 1124 so as to, e.g., effect closing of the jaws 1110a, 1110b.

The shaft 1104 can have a variety of sizes, shapes, and configurations. In an exemplary embodiment, the shaft 1104 can be rigid, e.g., made from a generally non-bendable material such as a metal (e.g., stainless steel, titanium, etc.) or a hard polymer. In other embodiments, the shaft 1104 can be configured to bend, such as being made from a generally flexible material, by including one or more articulation regions, etc. The shaft 1104 can have any longitudinal length, although in an exemplary embodiment it can be long enough to allow the handle portion 1102 to be manipulated outside a patient's body while the shaft 1104 extends through an opening in the body with the end effector 1106 disposed within a body cavity. In this way, the end effector 1106 can be easily manipulated when the device 1100 is in use during a surgical procedure. The shaft 1104 can have any diameter. For example, the shaft's diameter can be less than or equal to about 10 mm, e.g., less than or equal to about 7 mm, less than or equal to about 5 mm, etc., which can allow for insertion of the shaft 1104 through an minimally invasive access device, e.g., a trocar, a cannula, a multiport access device, etc., such as during a laparoscopic surgical procedure. The end effector 1106 coupled to the shaft's distal end can have a diameter equal to or less than the shaft's diameter, at least when the jaws 1110a, 1110b are in the closed position, which can facilitate insertion of the device's distal portion into a patient's body.

The end effector 1106 can have a variety of sizes, shapes, and configurations. In an exemplary embodiment, the end effector 1106 can be rigid. As shown in FIG. 2 and FIG. 3, the end effector 1106 including the first and second jaws 1110a, 1110b can be disposed at a distal end of the surgical device 1100. As in this illustrated embodiment, when the jaws 1110a, 1110b move between the open and closed positions, the second jaw 1110b can be configured to remain stationary relative to the shaft 1104, and the first jaw 1110a can be configured to move relative to the shaft 1104 and the second jaw 1110b by pivoting at the pivot joint 1108.

Figure 4:
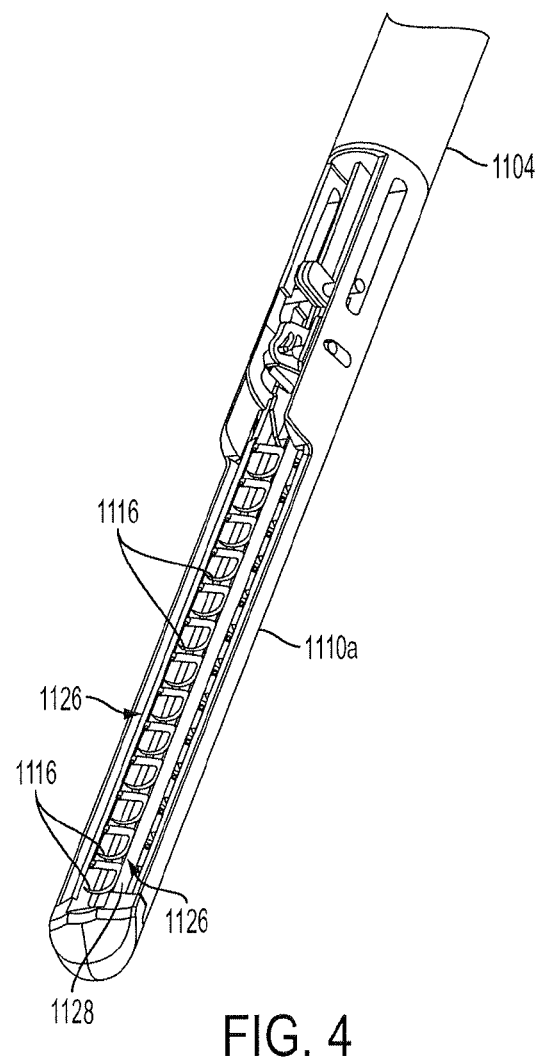
FIG. 4 is a perspective, partially cross-sectional view of the end effector and the cartridge of FIG. 3.

The end effector 1106 can be configured to releasably and replaceably seat a cartridge 1112 therein, as shown in FIG. 3 and FIG. 4. In this way, when the staples have been fired from the cartridge 1112, the cartridge 1112 can be removed from the second jaw 1110b and, optionally, replaced with another cartridge having another plurality of staples disposed therein. FIG. 2 shows the end effector 1106 without the cartridge 1112 seated therein. The end effector 1106 can be configured to receive the cartridge 1112 in the first jaw 1110a thereof, e.g., in a channel formed in the first jaw 1110a. The first jaw 1110a can be configured to seat cartridges of different sizes, thereby facilitating versatility of the device 1100.

Figure 5:
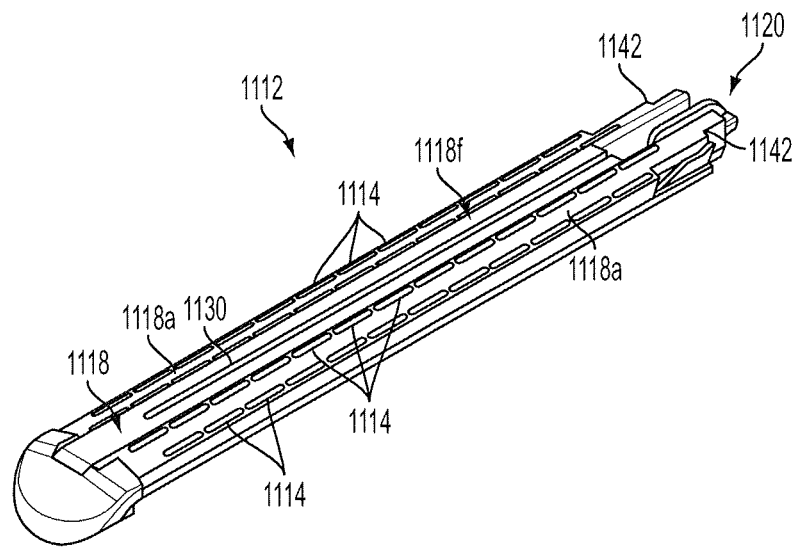
FIG. 5 is a perspective view of the cartridge of FIG. 3.
Figure 6:
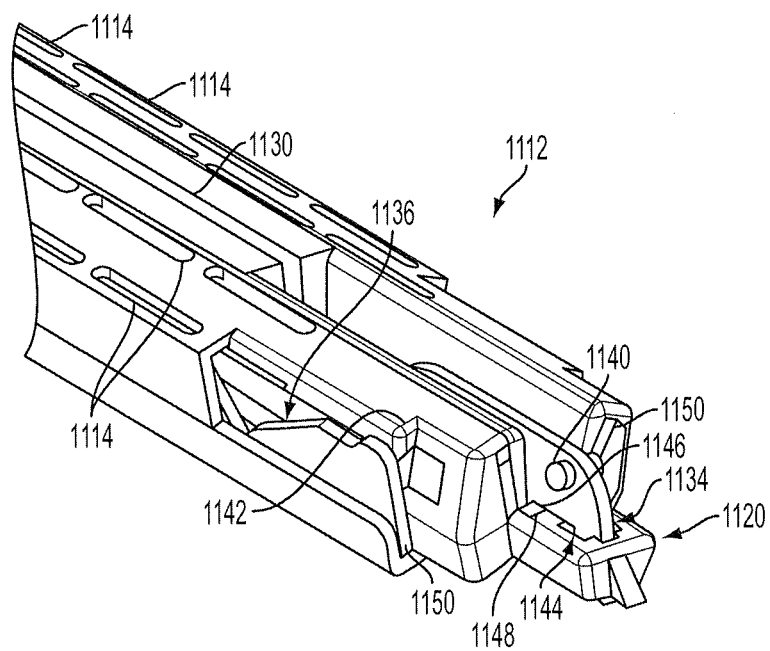
FIG. 6 is another perspective view of the cartridge of FIG. 3.
Figure 7:
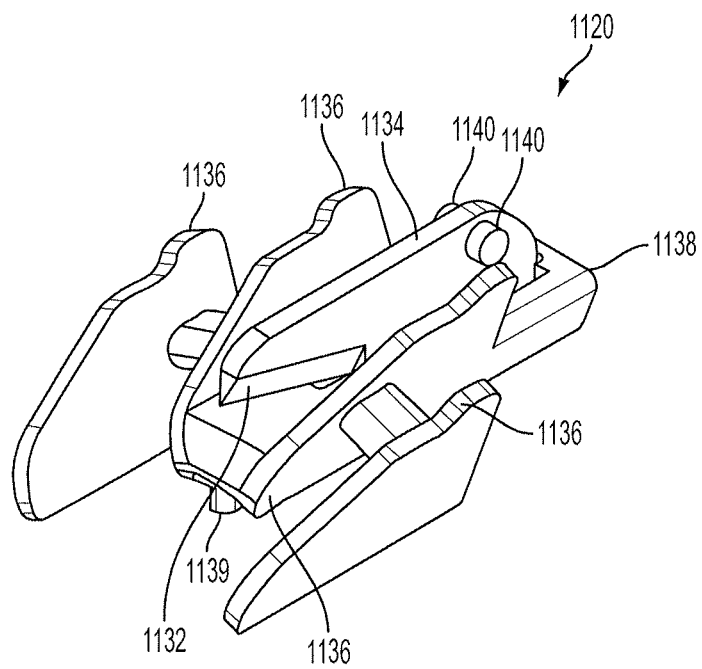
FIG. 7 is a perspective view of a sled of the cartridge of FIG. 3, the sled including a cutting element, and the cutting element being in a first position.
Figure 8:
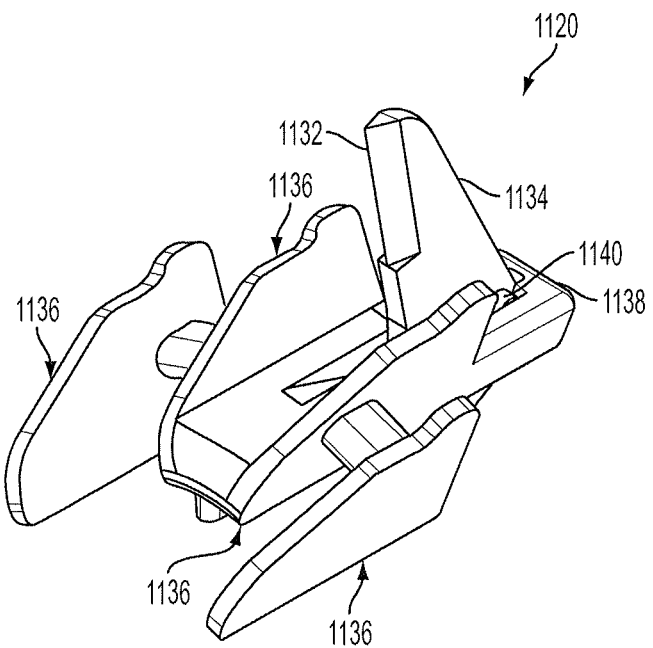
FIG. 8 is a perspective view of the sled of FIG. 7 with the cutting element in a second position that is different from the first position.

The cartridge 1112 can have a variety of sizes, shapes, and configurations, as will be appreciated by a person skilled in the art. As shown in FIG. 4, FIG. 5, and FIG. 6, the cartridge 1112 can include a sled 1120 and can have a plurality of staples 1116 disposed therein. The sled 1120 is also illustrated in FIG. 7 and FIG. 8. The cartridge 1112 can include a plurality openings 1114 formed in a tissue engaging surface 1118 thereof, as shown in FIG. 3, FIG. 5, and FIG. 6. The staples 1116 disposed in the cartridge 1112 can be configured to be ejected from the cartridge 1112 through the openings 1114, e.g., one staple 1116 out of each opening 1114 (as in this illustrated embodiment), two staples out of each opening 1114, etc. The openings 1114 can define staple-receiving recesses of the cartridge 1112 in which the staples 1116 are seated prior to being ejected from the cartridge 1112.

The staples 1116 can have a variety of sizes, shapes, and configurations. In this illustrated embodiment, the staples 1116 each have a D-shape and include a first leg that is substantially straight and a second leg that is curved. A person skilled in the art will appreciate that the first leg may not be precisely straight, e.g., due to manufacturing tolerances, but nevertheless be considered to be substantially straight. Each of the staples 1116 can be configured to be plastically deformable such that the staples 1116 can each be configured to change shape, such as when the staple 1116 is pressed against a tissue engaging surface (not shown) of the first jaw 1110a that faces the tissue engaging surface 1118 of the second jaw 1110b, while remaining a single unit, e.g., without either of the first and second legs breaking. A gap of space can exist between a terminal end of the first leg and a terminal end of the second leg. In other words, the "D" shape can have a gap therein. The gap of space can facilitate plastic deformation of the staple 1116.

The staples 1116 can each be frangibly attached to a carrier 1126, also referred to herein as a "carrier strip," disposed within the cartridge 1112. The staples 1116 can be frangibly attached to the carrier 1126 by, e.g., being stamped together with the carrier 1126 such that the staples 1116 and the carrier 1126 forms a single piece. The staples 1116 can each be configured to detach from the carrier 1126 when fired from the cartridge 1112. In some embodiments, some or all of the staples 1116 can be frangibly attached to another element, such as another element disposed within the cartridge 1112, an inner surface of the cartridge 1112, the tissue-engaging surface 1118 of the cartridge 1112, etc. The carrier 1126 can be fixedly attached to an upper surface of one or more rails 1128 defined by the cartridge 1112. The carrier 1126 can be configured to remain stationary relative to the cartridge 1112.

As shown in FIG. 3, FIG. 5, and FIG. 6, the cartridge 1112 can have a longitudinal slot 1130 formed therein. The longitudinal slot 1130 can extend along a substantially flat central portion 1118f of the tissue-engaging surface 1118. The slot 1130 can be configured to have a cutting element such as a knife (not shown) extend therethrough so as to be configured to cut tissue engaged by the tissue-engaging surface 1118, as discussed further below. The openings 1114 can be formed in angled portions 1118a of the tissue-engaging surface 1118 on both sides of the slot 1130, as shown in FIG. 3, FIG. 5, and FIG. 6. In some embodiments, the tissue-engaging surface 1118 can be substantially flat, e.g., not have angled portions, while in other embodiments, the tissue-engaging surface 1118 can be angled, e.g., not have any substantially flat portions.

As shown in FIG. 5 and FIG. 6, the cartridge 1112 can include a gap-setting feature 1142 configured to set of gap of space between the first and second jaws 1110a, 1110b when the jaws 1110a, 1110b are closed and the cartridge 1112 is seated in the second jaw 1110b. In this way, the gap-setting feature 1142 can be configured to define a minimum distance between the facing tissue-engaging surfaces of the first and second jaws 1110a, 1110b. The gap-setting feature 1142 can have a variety of sizes, shapes, and configurations. As in this illustrated embodiment, the gap-setting feature 1142 can include an indentation inward toward a lateral center of the cartridge 1112, where a portion of a lateral edge of the cartridge 1112 immediately proximal to the gap-setting feature 1142 is located laterally inward relative to a portion of a lateral edge of the cartridge 1112 located immediately distal to the gap-setting feature 1142.

The sled 1120 of the cartridge 1112 can have a variety of sizes, shapes, and configurations. The sled 1120 can be configured to translate longitudinally along the cartridge 1112 to cause deployment of the staples 1116 therefrom and to cause tissue engaged by the end effector 1106 to be cut with the cutting element extending through the slot 1130. The staples 1116 can be arranged longitudinally in the cartridge 1112, as shown in FIG. 4, and the sled 1120 can be configured to sequentially engage the longitudinally arranged staples 1116 as the sled 1120 translates longitudinally. As illustrated in FIG. 7 and FIG. 8, the sled 1120 can include a plurality of wedges 1136 and can include a cutting element 1134, which in this illustrated embodiment includes a knife with a blade 1132. The sled 1120 in this illustrated embodiment includes four wedges 1136 but the sled 1120 can include another number of wedges 1136 as appropriate for the arrangement of the staples 1116 in the cartridge 1112. Each of the wedges 1136 can have a shape configured to cause the staples 1116 contacted by that wedge 1136 to move upward toward the second jaw 1110b through the openings 1114 and deform against the second jaw 1110b. As shown in FIG. 6, the cartridge 1112 can include a plurality of longitudinal slots 1150 formed therein, each of the slots 1150 being configured to slidably receive one of the wedges 1136 therein. The slots 1150 can facilitate consistent, straight movement of the wedges 1136 through the cartridge 1112 to help ensure proper engagement of the wedges 1136 with the staples 1116.

Each of the wedges 1136 can be attached to a base 1138 of the sled 1120 and can be in a fixed position relative thereto. The base 1138 can have a guide element 1139 extending generally downward therefrom. The guide element 1139 can be configured to slide within a channel formed in the cartridge 1112 that includes the sled 1120. The cutting element 1134 can also be attached to the base 1138, but the cutting element 1134 can be configured to move relative to the base 1138. The cutting element 1134 can be substantially laterally centered in the base 1138, which can facilitate substantially central positioning of the cutting element 1134 relative to tissue engaged by the end effector 1106.

The cutting element 1134 can be configured to be movable relative to a remainder of the sled 1120 between a first position, shown in FIG. 7, and a second position, shown in FIG. 6 and FIG. 8. The first position can be an initial position of the cutting element 1134. In the first position, also referred to herein as a "stowed position," the blade 1132 can be generally obscured, e.g., oriented generally downward as shown in the embodiment of FIG. 4, FIG. 5, FIG. 6, and FIG. 7, which can help prevent the blade 1132 from inadvertent cutting, such as accidentally cutting a user of the device 1100 during seating of the cartridge 1120 within the end effector 1104 and/or premature cutting of tissue engaged by the end effector 1104. The base 1138 can have a cavity 1144 formed therein, as shown in FIG. 6, which can be configured to seat the cutting element 1134 at least partially therein when the cutting element 1134 is in the first position. In the second position, also referred to herein as an "upright position," the blade 1132 can be generally unobscured and facing a distal direction as shown in the embodiment of FIG. 6 and FIG. 8, which can allow the blade 1132 to extend through the slot 1130 and cut tissue engaged by the end effector 1106.

The sled 1120 can include a pivot member 1140 configured to facilitate movement of the cutting element 1134 relative to the remainder of the sled 1120. The pivot member 1140 can have a variety of sizes, shapes, and configurations. The pivot member 1140 can be attached to the cutting element 1134 such that engagement of the pivot member 1140 can cause the cutting element 1134 to pivot about a pivot point so as to move relative to the remainder of the sled. As in this illustrated embodiment the pivot member 1140 can include two separate pins extending laterally from opposite sides of the cutting element 1134. In other embodiments, the pivot member 1140 can include a single pin extending through the cutting element 1134 to extend laterally from opposite sides therefrom, a single pin extending laterally from one side of the cutting element 1134, etc. At the pivot point, the sled 1120 can include a pivot axle 1146 extending laterally from the cutting element 1134, and can include an axle cavity 1148 formed in the base 1138 and configured to receive the pivot axle 1146 therein.

The surgical devices described herein can be used in a variety of surgical procedures. In an exemplary embodiment, the procedure can be a minimally invasive procedure in which the surgical device can be advanced into a body of a patient through a relatively small opening in the patient. In a minimally invasive surgical procedure, one or more introducer devices (not shown), e.g., a cannula, a trocar, etc., can be advanced through an opening in the patient to provide access to a surgical site. A person skilled in the art will appreciate that one or more viewing devices, e.g., a scoping device such as an endoscope, can be advanced into the body through the incision or through another opening, e.g., another incision or a natural orifice, to provide visualization of the surgical site from outside the body. As will be appreciated by a person skilled in the art, the surgical device can be advanced into the patient's body in a variety of ways, such as by being inserted transorally therein, inserted through an introducer device, inserted through a scoping device, inserted directly through an incision, etc. Although the following embodiment of use of a surgical device in a surgical procedure is described with respect to the device 1100 of FIG. 1, any of the surgical devices described herein can be similarly used.

The surgical devices described herein can have any one or more variations to facilitate effective use of the device. Examples of such variations are described further below.

In some embodiments, a surgical device such as the above-mentioned surgical device 1100 can be configured to stabilize fasteners post-deployment. In general, the fasteners can be configured to resist counter rotation after being deployed. Fasteners can have a tendency to shift position relative to tissue that the fasteners are securing. The position shifting can be caused by any one or more factors, such as a type of the tissue, a thickness of the tissue, a shape of the fasteners (e.g., a curved shape thereof), and a strength of a bias urging a fastener into a certain position or configuration. The position shifting can take the form of counter rotation, in which the fastener rotates in a direction opposite to a direction in which the fastener was deployed into the tissue. This counter rotation can reduce the fastener's effectiveness in fastening the tissue because the fastener is "slipping" out of the tissue and/or reducing its hold on the tissue as a result of the counter rotation. The adverse effects of counter rotations can be exacerbated when, as in typical surgical procedures that use fasteners, a plurality of fasteners, all of which may all counter rotate to varying degrees, are deployed in tissue. The adverse effects of counter rotations can be exacerbated when tissue is relatively thick such that staples may not close to a great extent when deployed in the tissue. Fasteners being configured to resist counter rotation can help keep the staples secured in tissue into which the staples have been deployed, thereby helping to keep the tissue securely fastened and/or facilitating effective treatment of the tissue.

A fastener can be configured to resist counter rotation in a variety of ways. In the embodiments described below, staples are used as examples of fasteners, but as will be appreciated by a person skilled in the art, other types of fasteners can be similarly configured and used.

Figure 9:
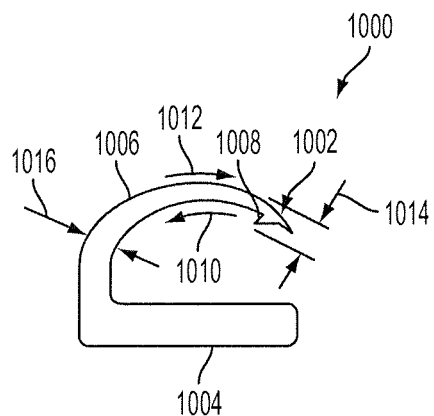
FIG. 9 is a side view of one embodiment of a fastener including an anti-rotation mechanism.

In some embodiments, a staple can include one or more anti-rotation mechanisms configured to resist counter rotation of the staple when the staple is deployed in tissue. FIG. 9 illustrates one embodiment of a staple 1000 that includes one or more anti-rotation mechanisms 1008 configured to resist counter rotation. The staple 1000 in this illustrated embodiment is generally configured like the previously described staples 1116 and has a D-shape with a pointed tip 1002, a first leg 1004 that is substantially straight and a second leg 1006 that is curved. The pointed tip 1002 can be a terminal end of the second leg 1006, as in this illustrated embodiment.

The staple 1000 can include one or more anti-rotation mechanisms 1008, which in this illustrated embodiment includes a barb 1008. This illustrated embodiment includes only one barb 1008, but the staple 1000 can include one or more barbs 1008 that are substantially identical to one another. The barb 1008 can be located in a variety of locations on the staple 1000. As in this illustrated embodiment, the one or more barbs 1008 can be formed on an inner-facing surface of the second leg 1006 at the pointed tip 1002. The barb 1008 can be oriented in a first direction 1010 that is opposite to a second direction 1012 in which the pointed tip 1002 points. The second direction 1012 can be the direction in which the staple 1000 is deployed into tissue, with the pointed tip 1002 leading the staple 1000 into the tissue. When the staple 1000 is deployed in the tissue, the barb 1008 can thus be configured to prevent counter rotation of the staple 1000 therein, thereby helping to retain the staple securely within the tissue.

The barb 1008 can have a variety of sizes. In an exemplary embodiment, the barb 1008 can have a maximum diameter 1014 is less than or substantially equal to a maximum diameter 1016 of the second leg 1006. In this way, a hole created by the barb 1008 when the barb 1008 penetrates into tissue can be less than or substantially equal to a hole created by the second leg 1006 when the second leg 1006 passes through the tissue, thereby helping to reducing any potential hemostasis issues that may arise from the barb 1008. The second leg 1006 can be tapered toward the pointed tip 1002 such that the maximum diameter 1016 of the second leg 1006 is adjacent a terminal end thereof that is opposite the pointed tip 1002.

Figure 10:
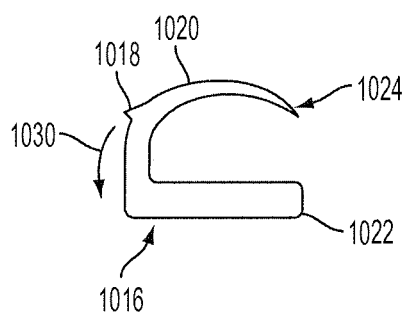
FIG. 10 is a side view of another embodiment of a fastener including an anti-rotation mechanism.
Figure 11:
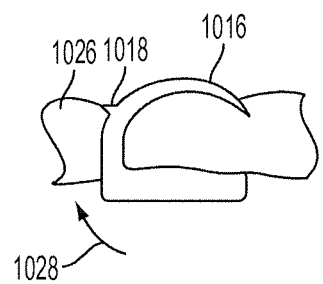
FIG. 11 is a side, partially transparent view of the fastener of FIG. 10 deployed in tissue.

FIG. 10 and FIG. 11 illustrate another embodiment of a staple 1016 that includes one or more anti-rotation mechanisms 1018 configured to resist counter rotation. The staple 1016 and the one or more anti-rotation mechanisms 1018, e.g., one or more barbs 1018, can be generally configured and used similar to the staple 1000 and the one or more barbs 1008, respectively, of FIG. 9. The one or more barbs 1018 in this illustrated embodiment, however, are formed in an intermediate portion of the staple's second leg 1020 between proximal and distal ends thereof, and the one or more barbs 1018 are formed on an outer-facing surface of a second leg 1020 of the staple 1016 that includes a pointed tip 1024 of the staple 1016 and that is connected to a first leg 1022 of the staple 1016.

FIG. 11 illustrates an embodiment of the staple 1016 as deployed in a tissue 1026. The staple 1016 can be deployed into the tissue 1026, e.g., fired from a cartridge such as the above-mentioned cartridge 1112, in a first direction 1028. The one or more barbs 1018 can be oriented in a second direction 1030 that is opposite to the first direction 1028, thereby helping to secure the staple 1016 to the tissue 1026 and helping to prevent counter rotation of the staple 1016 within the tissue 1026. The one or more barbs 1018 can be formed in the second leg's intermediate portion at a location substantially where the staple 1016 exits the tissue 1026, as in this illustrated embodiment. An exterior surface of the tissue 1026 can cooperate with the one or more barbs 1018 at such a location to help prevent counter rotation of the staple 1018, e.g., help prevent the staple 1016 from rotating in the second direction 1030 after being deployed in the tissue 1026.

Figure 12:
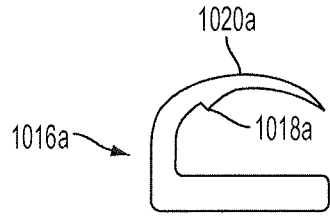
FIG. 12 is a side view of yet another embodiment of a fastener including an anti-rotation mechanism.
Figure 13:
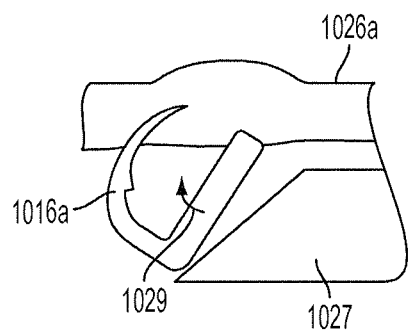
FIG. 13 is a side, partially transparent view of the fastener of FIG. 12 being deployed in tissue.

In another embodiment, the one or more barbs can be formed on an inner-facing surface of the second leg in addition to or in alternative to the one or more barbs formed on the outer-facing surface of the second leg. FIG. 12 illustrates such an embodiment of a staple 1016a with one or more barbs 1018a formed on an inner-facing surface of a second leg 1020a of the staple 1016a. The staple 1016a and the one or more anti-rotation mechanisms 1018a can be generally configured and used similar to the staple 1000 and the one or more barbs 1008, respectively, of FIG. 9. FIG. 13 illustrates an embodiment of the staple 1016a being deployed in a tissue 1026a by being pushed by a wedge 1027 of a sled so as to rotate the staple 1016a in a direction of an arrow 1029. FIG. 14 illustrates another embodiment of a staple 1016b with one or more barbs 1018b formed on an inner-facing surface of a second leg 1020b of the staple 1016b. The staple 1016b is like the staple 1016a of FIG. 12 except the staple 1016b of FIG. 14 includes at least one second anti-rotation mechanism 1017 on an outer-facing surface of the second leg 1020b. The at least one second anti-rotation mechanism 1017 in this illustrated embodiment include a plurality of spikes extending outward from the outer-facing surface of the second leg 1020b.

FIG. 15 and FIG. 16 illustrate another embodiment of a staple 1032 that includes one or more anti-rotation mechanisms 1034 configured to resist counter rotation. The staple 1032 and the one or more anti-rotation mechanisms 1034, e.g., one or more barbs 1034, can be generally configured and used similar to the staple 1000 and the one or more barbs 1008, respectively, of FIG. 9. The one or more barbs 1034 in this illustrated embodiment, however, are formed on an outer-facing surface of a second leg 1036 of the staple 1032 closer to a first leg 1037 of the staple 1032 than in the FIG. 9 embodiment, and are formed adjacent a terminal end of the second leg 1036 that is opposite to a terminal end thereof that includes a pointed tip 1038. In another embodiment, the one or more barbs can be formed on an inner-facing surface of the second leg 1036 in addition to or in alternative to the one or more barbs 1034 formed on the outer-facing surface of the second leg 1036.

FIG. 16 illustrates an embodiment of the staple 1032 deployed in a tissue 1040. The one or more barbs 1034 of the staple 1032 can be oriented similar to the one or more barbs 1026 of FIG. 10 and FIG. 12 so as to be oriented in a direction that is opposite to a direction in which the staple 1032 was deployed into the tissue 1040. The one or more barbs 1034 can be formed on the second leg 1036 at a location disposed within the tissue 1040 when the staple 1032 is within the tissue 1040, as in this illustrated embodiment. The tissue 1040 can thus completely surround the one or more barbs 1034 so as to help the one or more barbs 1034 prevent counter rotation.

In some embodiments, an anti-rotation mechanism of a first staple can be configured to engage a second staple deployed adjacently thereto in tissue. The anti-rotation mechanism can be configured to help prevent counter rotation of the first and second staples. In an exemplary embodiment, an anti-rotation mechanism of a staple configured to engage an adjacent staple can be in the form of a coupling element configured to receive a pointed tip of the adjacent staple when both of the staples are deployed in tissue.

FIG. 17 illustrates one embodiment of a staple 1042 that includes an anti-rotation mechanism 1044 in the form of a coupling element configured to engage an adjacently deployed staple. The staple 1042 in this illustrated embodiment is generally configured and used like the previously described staples 1116 and has a D-shape with a pointed tip 1046, a first leg 1048 that is substantially straight and a second leg 1050 that is curved. The pointed tip 1046 can be a first terminal end of the second leg 1050, as in this illustrated embodiment. The anti-rotation mechanism 1044 can be formed on an outer-facing surface of the staple 1042 and can be located at a junction of the first and second legs 1048, 1050. The anti-rotation mechanism 1044 can include a ring or hoop configured to receive a pointed tip of an adjacent staple therein. The pointed tip can extend partially or all the way through a hole 1052 defined by the anti-rotation mechanism 1044. The anti-rotation mechanism 1044 having the adjacent staple's tip at least partially captured by the anti-rotation mechanism 1044 can help prevent counter rotation of the staple 1042 as well as the adjacent staple engaged by the staple 1042. Because the staple 1042 can be rotated to be deployed in tissue and can be one of a plurality of staples deployed in a longitudinal row, as discussed herein, the staple's tip 1046 can rotate into a previously deployed staple's anti-rotation mechanism. In this way, staples deployed in the longitudinal row can all be interconnected with one another via the anti-rotation mechanisms, thereby helping to stabilize the entire row of staples in tissue.

FIG. 18 illustrates a plurality of staples 1042a, 1042b, 1042c, each similar to the staple 1042 of FIG. 17, having been deployed such that a pointed tip of a staple is captured as it rotates by an anti-rotation mechanism of the one of the staples having been deployed immediately prior thereto. In other words, a pointed tip 1046b of the staple 1042b deployed second has been captured by an anti-rotation mechanism 1044a of the staple 1042a deployed first, and a pointed tip 1046c of the staple 1042c deployed third has been captured by an anti-rotation mechanism 1044b of the staple 1042b deployed second. As shown in this illustrated embodiment, a pointed tip 1046a of the first staple 1042a can not be coupled to an anti-rotation mechanism, and an anti-rotation mechanism of a last one of the deployed staples 1042c can not be coupled to another staple. Only three staples 1042a, 1042b, 1042c are shown in this illustrated embodiment, but nay number of staples can be so interconnected using anti-rotation mechanisms.

FIG. 19 illustrates another embodiment of a staple 1054 that includes an anti-rotation mechanism 1056 in the form of a coupling element configured to engage an adjacently deployed staple. The staple 1054 in this illustrated embodiment is generally configured and used like the staple 1042 of FIG. 17 except that the staple 1054 includes a second anti-rotation mechanism 1058. The second anti-rotation mechanism 1058 in this illustrated embodiment a pointed tip 1060 of the staple 1056 having a barb similar to the barb 1008 of FIG. 9. The second anti-rotation mechanism 1058 in the form of a barb can be configured to help hold the staple 1054 in tissue and can be configured to help prevent the pointed tip 1060 from de-coupling from an adjacent staple's anti-rotation mechanism, e.g., from moving out of a hole of a ring or loop once advanced therein. FIG. 19 also shows an adjacent staple 1054a (partially illustrated), which is generally configured and used similar to the staple 1054, with its pointed tip 1060a and second anti-rotation mechanism 1058a engaged by the anti-rotation mechanism 1056 of the staple 1054.

In some embodiments, an orientation of a fastener relative to an orientation of one or more fasteners deployed adjacent thereto can be configured to help prevent counter rotation. In an exemplary embodiment, fasteners in one longitudinal row can all face in a first direction, e.g., proximally, and fasteners in a longitudinal row adjacent thereto can all face in an opposite direction, e.g., distally. In this way, forces exerted on tissue in which the fasteners facing opposite directions are deployed can help hold the fasteners in the tissue.

Figure 20:
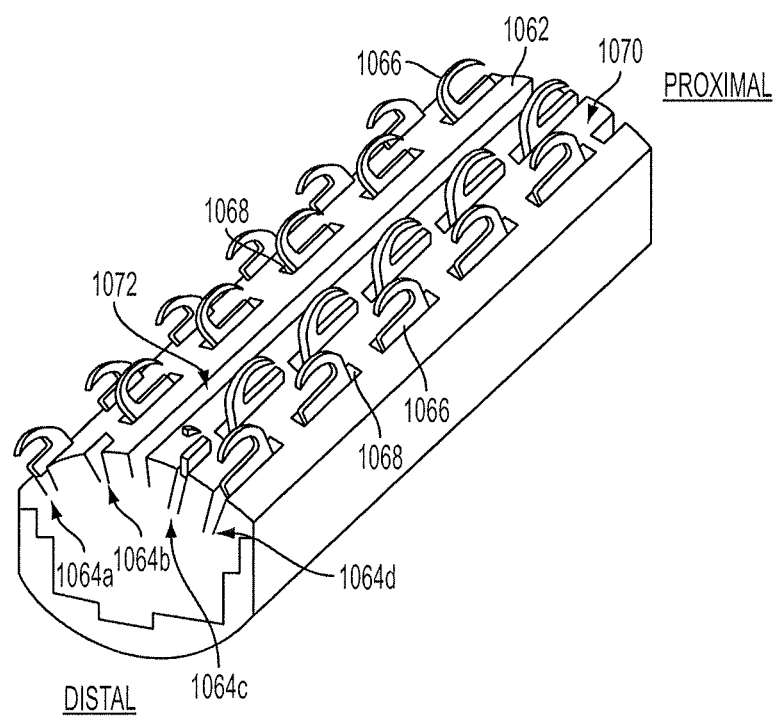
FIG. 20 is a perspective view of an embodiment of a cartridge and staples that can be deployed therefrom in opposite-facing longitudinal rows.

FIG. 20 illustrates one embodiment in which a cartridge 1062 has staples 1066 in adjacent longitudinal rows facing in opposite directions. The staples 1066 are shown deployed out of the cartridge 1062 for ease of explanation. The cartridge 1062 in this illustrated embodiment has first, second, third, and fourth longitudinal rows 1064a, 1064b, 1064c, 1064d rows of staples 1066. The staples 1066 in the first and fourth rows 1064a, 1064d can face a first direction, e.g., a distal direction, when deployed, and the staples 1066 in the second and third rows 1064b, 1064c can face a second, opposite direction, e.g., a proximal direction, when deployed. In this way, when the staples 1062 are in tissue, the adjacent first and second rows 1064a, 1064b of staples 1066 can face opposite directions, and the adjacent third and fourth rows 1064c, 1064d of staples 1066 can face opposite directions. A cutting element (not shown) can extend through a longitudinal slot 1072 in the cartridge 1062 and cut tissue between the second and third rows 1064b, 1064c as discussed herein such that the second and third rows

1064*b*, 1064*c* having staples 1066 facing the same direction generally will not affect counter rotation.

As discussed herein, the staples 1066 can be deployed from the cartridge 1062 by rotating out of openings 1068 formed in the cartridge's tissue-engaging surface 1070. Typically, all staples in a cartridge are deployed as a sled moves longitudinally through the cartridge, e.g., as the sled translates distally. However, the staples 1066 facing in opposite directions can be deployed in two passes of a sled through the cartridge 1062, one pass in which the sled translates distally to deploy the staples 1066 facing in one direction and another pass in which the sled translates proximally to deploy the staples facing the opposite direction.

Figure 21:
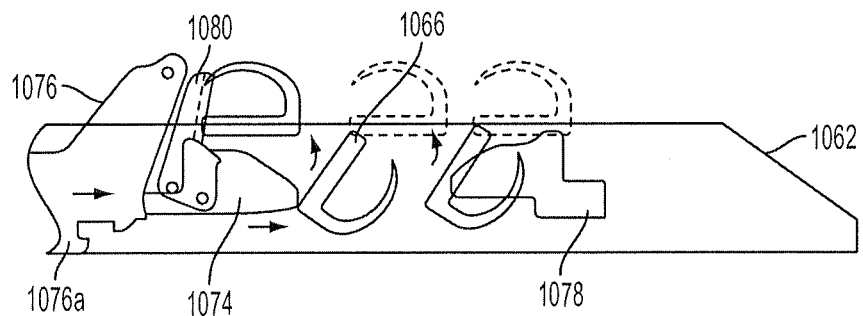
FIG. 21 is a side, partially transparent view of the staples of FIG. 20 that face in one direction being deployed from the cartridge with a drive beam engaged with a first sled translating distally through the cartridge.
Figure 23:
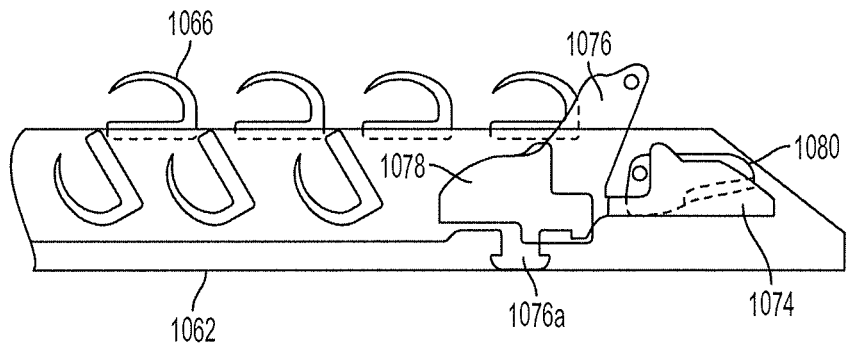
FIG. 23 is a side, partially transparent view of the drive beam engaged with the second sled of FIG. 22 and disengaged from the first sled.
Figure 24:
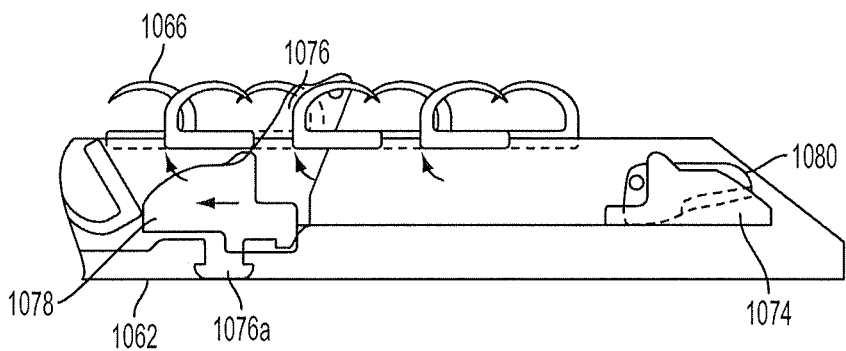
FIG. 24 is a side, partially transparent view of the staples of FIG. 23 facing in an opposite direction being deployed from the cartridge with the drive beam engaged with a second sled translating proximally through the cartridge.
Figure 25:
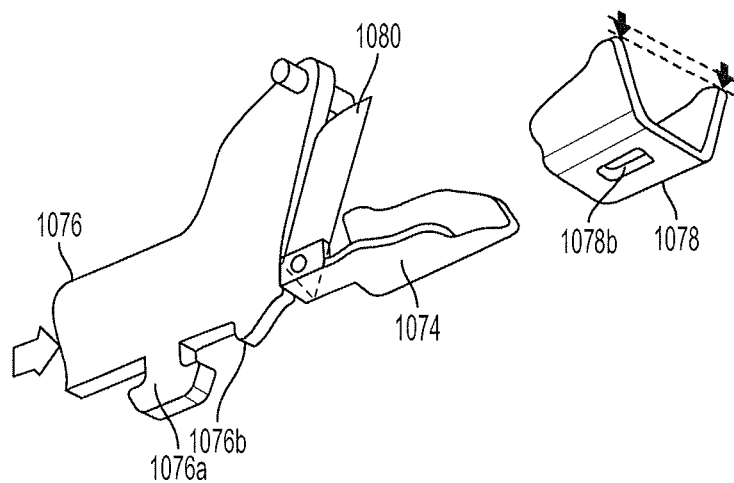
FIG. 25 is a perspective view of the drive beam and the first sled of FIG. 24 coupled together and moving distally, and a perspective view of second sled not coupled to and positioned distal to the drive beam and the first sled.

FIG. 21, FIG. 22, FIG. 23, and FIG. 24 illustrate one embodiment of deploying the staples 1066 that face in opposite directions using a first sled 1074, a drive beam 1076 (also referred to herein as a "drive rod" and an "I-beam"), and a second sled 1078, which are also shown in FIG. 25, FIG. 26, FIG. 27, and FIG. 28. Although this illustrated embodiment shows deployment of the staples 1066 disposed in the cartridge 1062, other staples disposed in other cartridges in facing opposite direction can be similarly deployed. The relative positions of the first sled, drive beam 1076, and second sled 1078 in FIG. 25, FIG. 26, FIG. 27, and FIG. 28 correspond respectively to their positions in FIG. 21, FIG. 22, FIG. 23, and FIG. 24. The first sled 1074 can be generally configured and used similar to the previously described sled 1120. The first sled 1074 can include a cutting element 1080, which includes a knife in this illustrated embodiment. The cutting element 1080 can be configured to pivot between a stowed position in which the cutting element's blade 1082 is generally obscured, as shown in FIG. 22, FIG. 23, FIG. 24, FIG. 26, FIG. 27, and FIG. 28, and an upright position in which the cutting element 1080 extends through the slot 1072 such that the blade 1082 can cut tissue, as shown in FIG. 21 and FIG. 25.

As shown in FIG. 21 and FIG. 25, the second sled 1078 can be parked in an initial position near a distal end of the cartridge 1062. The drive beam 1076 can be advanced distally, e.g., by manipulating a handle of a surgical device including the cartridge 1062 seated in an end effector thereof, so as to cause the cutting element 1080 to move from the stowed position to the upright position and so as to push the first sled 1074 distally. The drive bean 1076 can include a guide member 1076*a* configured to slide within a corresponding guide track (not shown) formed in the cartridge 1062, which can help the drive beam 1076 translate straight and smoothly within the cartridge 1062. The distal movement of the first sled 1074 can cause the second and third rows 1064*b*, 1064*c* of staples 1066 to be deployed.

Figure 22:
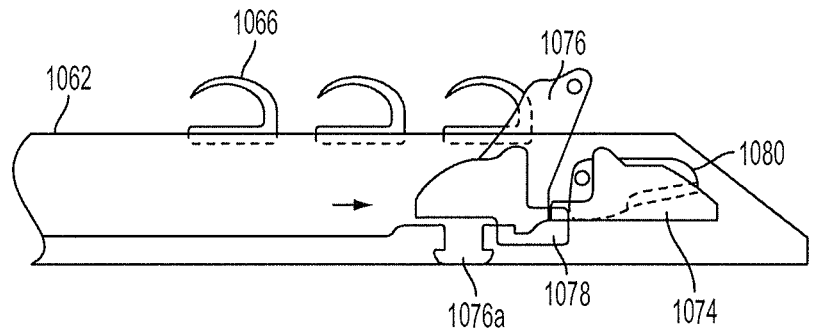
FIG. 22 is a side, partially transparent view of the first wedge sled of FIG. 21 at a distal end of the cartridge and passing over a second sled.
Figure 26:
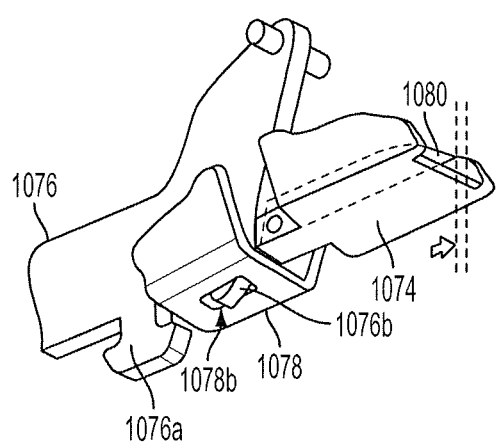
FIG. 26 is a perspective view of the drive beam and the first sled of FIG. 22 coupled together and the first sled passing by the second sled.
Figure 27:
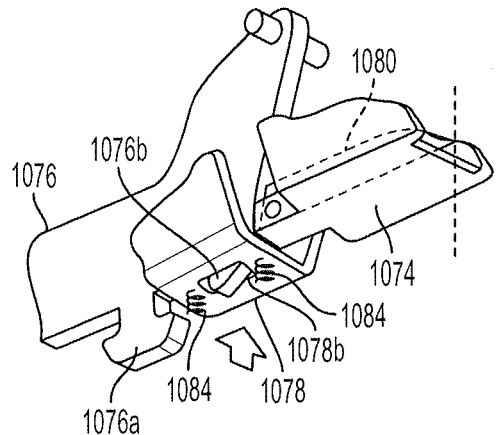
FIG. 27 is a perspective view of the drive beam and the second sled of FIG. 23 coupled together and a perspective view of first sled not coupled to and positioned distal to the drive beam and the second sled.
Figure 28:
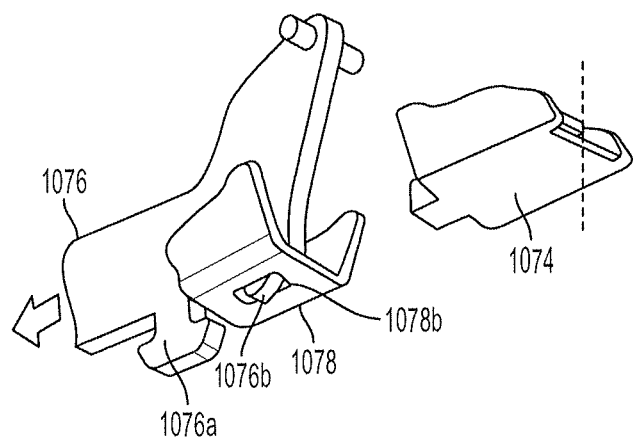
FIG. 28 is a perspective view of the drive beam and the second sled of FIG. 24 coupled together and moving proximally, and a perspective view of first sled not coupled to and positioned distal to the drive beam and the second sled.

After deploying the staples 1066 in the second and third rows 1064*b*, 1064*c*, the distally advancing first sled 1074 can advance distally beyond the parked second sled 1078, as shown in FIG. 22 and FIG. 26, and the drive rod 1076 can engage the parked second sled 1078, as shown in FIG. 23 and FIG. 27. The drive rod 1076 can engage the second sled 1078 in a variety of ways. As in this illustrated embodiment, the drive rod 1076 can include a protrusion 1076*b* extending therefrom and configured to engage a corresponding opening 1078*b* formed in the second sled 1078. The first sled 1076 being advanced to its distal-most position relative to the cartridge 1062 can cause a spring 1084, shown in FIG. 27, to be released. The spring 1084 can be coupled to the second sled 1078 and can be biased upward such that release of the spring 1084 can cause the second sled 1078 to move upward, thereby allowing the protrusion 1076*b* to engage the opening 1078 as shown in FIG. 23 and FIG. 27. The drive rod 1076 can be advanced proximally, e.g., by manipulating the handle of the surgical device, so as to cause the second sled 1078 engaged with the drive rod 1076 to move from the parked position and be advanced proximally with the drive rod 1076 due to the engagement of the protrusion 1076*b* and the opening 1078*b*. As shown in FIG. 25 and FIG. 28, the proximal movement of the second sled 1078 can cause the first and fourth rows 1064*a*, 1064*d* of staples 1066 to be deployed. The first sled 1074 can be parked near the distal end of the cartridge 1062 during the drive beam's and second sled's proximal movement, as also shown in FIG. 24 and FIG. 28. In this illustrated embodiment, the tissue is thus cut before all of the staples 1066 have been deployed since the tissue is cut by the cutting element 1080 during firing of the staples 1066 in the second and third rows 1064*b*, 1064*c* and prior to firing of any of the staples in the first and fourth rows 1064*a*, 1064*d*.

Two-pass deployment of the staples 1066 in which a first portion of the staples 1066 are deployed in one pass, e.g., a distal pass of the drive beam 1076, and a second, remaining portion of the staples 1066 are deployed in a second pass, e.g., a proximal pass of the drive beam 1076, can reduce a force needed to fire the staples 1066. A first force can be required to deploy the staples 1066 in the first pass, and a second force can be required to deploy the staples 1066 in the second pass. In this way, instead of requiring a sum of the first and second forces to deploy all of the staples 1066, two smaller forces can be applied to deploy all of the staples. These reduced forces for firing can make firing of staples much easier in devices having relative small diameters, such as those used in minimally invasive surgical procedures. For example, it can be difficult to generate a force required to deploy staples from an end effector of a 5 mm device, so effectively dividing the force required in half by having two passes can make the device easier to use and/or more effective in deploying staples properly.

In another embodiment of deploying staples from a cartridge in which some of the staples are disposed therein facing one direction and a remainder of the staples are disposed therein facing another, opposite direction, a sled can be configured to advance distally through the cartridge so as to cause deployment of all of the staples. In other words, the sled's distal movement can be configured to cause deployment of staples facing in opposed directions. Such a sled can include sides that extend upward and downward on left and right sides thereof so as to allow movement of the sled in one direction to cause deployment of staples facing in opposite directions.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical fastening device, comprising:
   an elongate shaft having an end effector coupled to a distal end thereof, the end effector including
   first and second opposed jaws coupled to one another and configured to engage tissue therebetween, and
   a staple cartridge disposed within the first jaw, the staple cartridge including a plurality of D-shaped, plastically deformable staples, each staple being configured to rotate in a first direction into tissue engaged between the first and second jaws, and each staple having an anti-rotation mechanism configured to prevent rotation in a second direction opposite to the first direction when the staples are deployed in tissue, wherein each D-shaped staple includes a first leg that is substantially straight and a second leg that is curved, and the anti-rotation mechanism on each staple comprises a hoop formed adjacent to an intersection between the first and second legs and configured to receive a tip of the first leg when the staples are deployed in tissue.

2. The device of claim 1, wherein the anti-rotation mechanism is configured to receive the tip such that counter-rotation of the staples is prevented.

3. The device of claim 1, wherein the plurality of staples are frangibly attached to a carrier.

4. The device of claim 1, wherein the plurality of staples are arranged in longitudinal rows.

5. The device of claim 1, further comprising a sled slidable through the first jaw such that the sliding of the sled causes each of the staples to rotate into tissue engaged between the first and second opposed jaws.

6. A surgical fastening device for treating tissue, comprising:
   a handle;
   an elongate shaft extending distally from the handle;
   an end effector coupled to a distal end of the elongate shaft, the end effector having a jaw and an anvil pivotally connected to the jaw, the jaw and the anvil being configured to engage tissue therebetween;
   a plurality of fasteners disposed within the jaw, the fasteners being rotatable about a pivot point; and
   a sled slidable through the jaw such that distal advancement of the sled causes each of the plurality of fasteners to rotate into tissue engaged between the jaw and the anvil;
   wherein each fastener include an anti-rotation feature configured to prevent counter-rotation of the fasteners when deployed in tissue; and
   wherein the anti-rotation feature comprises a coupling element formed on each fastener and configured to receive a tip of an adjacent fastener when deployed such that counter-rotation of the fasteners is prevented, and the coupling element comprises a hoop formed on the fastener.

7. The device of claim 6, wherein the plurality of fasteners are frangibly attached to a carrier.

8. The device of claim 6, wherein the plurality of fasteners are arranged in longitudinal rows.

9. The device of claim 6, wherein the plurality of fasteners are plastically deformable from a first configuration to a second configuration.

10. The device of claim 6, wherein each of the plurality of fasteners is substantially D-shaped.

* * * * *